(12) United States Patent
Schulze-Forster et al.

(10) Patent No.: US 8,425,877 B2
(45) Date of Patent: Apr. 23, 2013

(54) METHOD FOR DIAGNOSIS OF SYSTEMIC SCLEROSIS INVOLVING AN ANTI-AT1-RECEPTOR ANTIBODY

(75) Inventors: Kai Schulze-Forster, Teltow (DE); Harald Heidecke, Berlin (DE)

(73) Assignee: CellTrend GmbH, Luckenwalde (DE)

( * ) Notice: Subject to any disclaimer, the term of this patent is extended or adjusted under 35 U.S.C. 154(b) by 0 days.

(21) Appl. No.: 12/376,164

(22) PCT Filed: Jul. 31, 2007

(86) PCT No.: PCT/EP2007/057910
§ 371 (c)(1),
(2), (4) Date: Nov. 6, 2009

(87) PCT Pub. No.: WO2008/015218
PCT Pub. Date: Feb. 7, 2008

(65) Prior Publication Data
US 2010/0098688 A1 Apr. 22, 2010

(30) Foreign Application Priority Data
Aug. 4, 2006 (EP) .................................... 06016296

(51) Int. Cl.
*A61K 49/00* (2006.01)
*A61K 39/395* (2006.01)
*G01N 33/564* (2006.01)

(52) U.S. Cl.
USPC .......... 424/9.1; 424/130.1; 436/507; 514/16.3

(58) Field of Classification Search ........................ None
See application file for complete search history.

(56) References Cited

U.S. PATENT DOCUMENTS

| | | | |
|---|---|---|---|
| 7,745,139 B1* | 6/2010 | Wallukat et al. ................ | 435/7.1 |
| 2003/0078190 A1 | 4/2003 | Weinberg | |
| 2004/0192634 A1 | 9/2004 | Schulze-Forster et al. | |
| 2005/0014200 A1* | 1/2005 | MacVicar ....................... | 435/7.2 |
| 2006/0135422 A1 | 6/2006 | Moskowitz | |
| 2006/0263835 A1 | 11/2006 | Wallukat | |
| 2010/0075348 A1 | 3/2010 | Schulze-Forster et al. | |

FOREIGN PATENT DOCUMENTS

| | | |
|---|---|---|
| CA | 2363999 A1 | 6/2000 |
| DE | 19954305 A1 | 6/2000 |
| EP | 0480381 | 4/1992 |
| EP | PCT/EP2007/057911 | 7/2007 |
| WO | WO 0037075 | 6/2000 |
| WO | WO 0039154 | 7/2000 |
| WO | 0210753 A | 2/2002 |
| WO | WO 0210753 | 2/2002 |
| WO | 02093171 A2 | 11/2002 |
| WO | WO2004/051280 | 6/2004 |
| WO | WO 2006/060336 | 6/2006 |
| WO | 2008015218 R | 5/2008 |
| WO | PCT/EP/2007057910 R | 5/2008 |

OTHER PUBLICATIONS

Wallukat et al., Patients with preeclampsia develop agonistic auto antibodies against the angiotensin AT1 receptor, J. Clin. Investig. 103, 945-952, 1999.*
Dragun et al., Angiotensin II Type 1-Receptor Activating Antibodies in Renal-Allograft Rejection, The New England Journal of Medicine, 352, 558-569, 2005.*
Liao et al., Auto antibodies against AT1-Receptor and a1-AdrenergicReceptor in Patients with Hypertension, Hypertension Res. 25, 641-646, 2002.*
Cobankara, Veli et al. "Renin and Angiotensin-Converting Enzyme (ACE) as Active Components of the Local Synovial Renin-Angiotensin System in Rheumatoid Arthritis." Rheumatology International vol. 25 No. 4 (May 1, 2005): 285-291.
Walsh, David et al. "AT1 Receptor Characteristics of Angiotensin Analogue Binding in Human Synovium." British Journal of Pharmacology vol. 112 No. 2. (Jun. 1, 1994): 435-442.
Pitotti et al., "HPLC method for evaluation of urinary angiotensin-converting enzyme: some examples of normal subjects and patients with renal transplantation", Journal of Pharmaceutical and Biomedical Analysis, vol. 4, No. 5, 677-683,1986.
Colonna et al., "Non-Renin Dependent Hypertension in Renal Allograft Rejections, A structural and functional analysis," Archives of Pathology & Laboratory Medicine, vol. 108, Nr. 2, pp. 117-120, Feb. 1984.
Oldfield et al., "Efferent Neural Projections of Angiotensin Receptor (AT1) Expressing Neurons in the Hypothalamic Paraventricular Nucleus of the Rat" Joural of Neuroedocrinology. vol. 13, No. 2, pp. 139-146, 2001.
Inigo et al., "Effects of losartan and amlodipine on intrarenal hemodynamics and TGF-beta1 plasma levels in a crossover trial in renal transplant receipients" Journal of the American Society of Nephrology, vol. 12, pp. 822-827, 2001.

(Continued)

*Primary Examiner* — Elly-Gerald Stoica
(74) *Attorney, Agent, or Firm* — Parker Highlander PLLC (57) ABSTRACT

The present invention relates to a method for diagnosis of a disease selected from the group of diabetes, vasculitis, collagenosis, an inflammatory rheumatic disease and arteriosclerosis wherein, presence or absence of an anti-$AT_1$-receptor antibody is determined in a sample from a patient to be diagnosed and wherein, the presence of an anti-$AT_1$-receptor antibody is indicative of the disease. The invention further relates to the use of an inhibitor of an anti-$AT_1$-receptor antibody or an inhibitor of an $AT_1$-receptor for the production of a medicament as well as plasmapheresis of blood for the removal of anti-$AT_1$-receptor antibodies.

13 Claims, 3 Drawing Sheets

OTHER PUBLICATIONS

Fu et al., "Autoantibodies against the angiotensin receptor (AT1) in patients with hypertension" Journal of Hypertension, vol. 18, pp. 945-953, 2000.

Dechend et al., "AT1 receptor agonistic antibodies from preeclamptic patients cause vascular cells to express tissue factor" Circulation, vol. 101, pp. 2382-2387, 2000.

Bachy et al., "Hypertension after renal transplantation" British Medical Journal, vol. 2, pp. 1287-1289, 1976.

Benigni, et al, "Endothelin Antagonists", The Lancet, vol. 353, 133-136, Jan. 9, 1999.

Haas, "Pulmonary Hypertension Associated with Systemic Lupus Erythematosus", Bulletin of the Nationai Academy of Medicine, Netherlands, 2004, vol. 188, No, 6, 985-907, Medline/NLM English Abstract 1 page (XP-002415918).

McLaughlin, "Pulmonary Arterial Hypertension: Current Diagnosis and Management", ACC Current Journal Review, May 6, 2002, 17-21, 11:3.

Morris, et al., "Specific, inhibition of the endothelin A receptor with ZD4054: clinical and pre-clinical evident", British Journal of Cancer, 2005-2006, 2148-2152. 92:12.

O'Callaghan, et al, "Sitaxsenten: an endotheiin-A receptor antagonist for the treatment of pulmonary arterial hypertension", International Journal of Clinical Practice, 2006-2004, 475-481, 60:4.

Plan, "Acquisitions recentes en rhumatisiogie", Medecine & Hygiene, Oct. 2, 2002, 1803-1606, 60:2407.

Plan, "Acquisitions recentes en rhumatoiogie"Medecine & Hygiene, Oct. 2, 2002, 1803-1808, 60:2407, English Translation.

Suzuki, et al., "A Sensitive Sandwich-Enzyme Immunoassay for Human Endothelin", Journal of Immunological Methods, 1989: vol. 118, 245-250.

Perez, "Appreciating the Heterogeneity in Autoimmune Disease: Multiparameter Assessment of Intracellular Signaling Mechanisms", Ann. N.Y. Acad. Sci., 2005, 1062:155-164.

Election/Restriction Requirement, dated Apr. 12, 2011, Issued in U.S. Appl. No. 12/376,200, 8 pages.

Non-Final Office Action, dated Jul. 12, 2011, Issued in U.S. Appl. No. 12/376,200, 9 pages.

Non-Final Office Action, dated Dec. 28, 2011, Issued in U.S. Appl. No. 12/376,208, 7 pages.

Non-Final Office Action, dated Aug. 13, 2012, issued in U.S. Appl. No. 12/376,200, 13 pages.

Ortmann J., et al., "Endothelin inhibition delays onset of hyperglycemia and associated vascular injury in type I Diabetes: Evidence for endothelin release by pancreatic islet $\beta$-cells, " Biochem, Biophys. Res. Comm., vol. 334, 2005, pp. 689-695.

Schiffrin E.L., "Vascular endothelin in hypertension," Vascular Pharmacol., vol. 43, 2005, pp. 19-29.

Amman K., et al., "Blood Pressure-Independent Additive Effects of Pharmacologic Blockade of the Renin-Angiotensin and Endothelin Systems on progression in a Low-Renin Model of Renal Damage, " J. Am. Soc. Neprol, vol. 12, 2001, pp. 2571-2584.

Thway T.M., et al. "Antibodies from preeclamptic patients stimulate increased intracellular Ca2 + mobilization through angiotensin receptor activation," Sep. 21, 2004, Circulation, vol. 110. No. 12, pp. 1612-1619.

Dalbeth N., et al., The non-thiol angiotensin-converting enzyme inhibitor quinapril suppresses inflammatory arthritis, Reurnatology, Oxford Unviersity Press, London, GB, vol. 44, No. 1, Jan. 2005, pp. 24-31.

Cheng Zhong Jian, et al., "Angiotensin II and vascular inflammation, " Medical Science Monitor: International Medical Journal of Experimental and Clinical Research June 2005, vol. 11, No. 6, June 2005, pp. RA194-RA205.

Ruiz-Ortega M., et al., "Proinflammatory actions of angiotensins," Current Opinion in Nephrology and Hypertension, May 1, 2001, pp. 321-329.

Gohjl K., et al., "Expression of endothelin receptor A associated with prostate cancer progression," Journal of Urology, Baltimore, MD, US, vol. 165, No. 3, March 2001, pp. 1033-1036.

* cited by examiner

METHOD FOR DIAGNOSIS OF SYSTEMIC SCLEROSIS INVOLVING AN ANTI-AT1-RECEPTOR ANTIBODY

In medicine, vasculitis (plural: vasculitides) is a group of diseases featuring inflammation of the wall of blood vessels due to leukocyte migration and resulting damage. While most vasculitides are rare, they generally effect several organ systems and can cause severe disability. Vasculitides are classified into the large vessel vasculitis such as Takayasu arteritis and giant cell (temporal) arteritis. Further, medium vessel vasculitis, such as polyarteritis nodosa and Kawasaki disease. Small vessel vasculitis such as Churg-Strauss arteritis, Wegener's granulomatosis and hypersensitivity vasculitis.

Patients usually present with systemic symptoms with single or multi organ dysfunction. Common (and nonspecific) complaints include fatigue, weakness, fever, arthralgias, abdominal pain, hypertension, renal insufficiency, a neurologic dysfunction. The following symptoms should raise a strong suspicion of vasculitis, however, the diagnosis is difficult. These symptoms are monoeuritis multiplex, palpable purpura and pulmonary-renal.

A detailed history is important to a elicit any recent medications, any risk of hepatitis infection or any recent diagnosis with a connective tissue disorder such as SLE. Diagnosis may include an antinuclear antibody (ANA) test which detects an underlying connectivity tissue disorder, especially SLE. Diagnosis may also include antineutrophil cytoplasmic antibody (ANCA) which may suggest Wegener's granulomatosis, polyarteritis nodosa, Chrug-Strauss-Syndrome or drug-induced vasculitis, but is not diagnostic. The only safer way of diagnosing vasculitis is a tissue biopsy which at present is the "gold standard" of diagnosis.

Thus, there is a need for a diagnostic tool for diagnosing vasculitis. Further, there is a need for a medicament for the treatment of vasculitis.

Collagenosis is the term for a group of rare autoimmune diseases. Here the body creates anti-bodies against parts of the connective tissue. Collagenosis are diseases such as SLE, systemic lupus, Wegener granulomatosis, CREST-Syndrome and SHARP-Syndrome. Collagenosis is difficult to diagnose. Thus, there is a need for a tool for diagnosis collagenosis.

Approximately 100 million people in Europe suffer from some form of inflammatory or degenerative rheumatic disease causing the impact of rheumatic diseases on European societies to be overwhelming for society. Joint diseases account for half of all chronic conditions in persons aged 65 and over.

The quality of life of approximately 7.5% of the European population is severely and permanently reduced by pain and functional impairment caused by rheumatic diseases. Immobility and reduced life expectancy are the most drastic consequences of these at present, incurable diseases. In Europe alone, rheumatic disease impose an economic burden of more than 200 billion EUR per year. Indeed, the impact of rheumatic diseases in a social and economic burden will increase dramatically as the European population ages. A new therapy is targeting the molecules involved in the pathogenesis of chronic inflammatory disease have been developed in recent years. Despite these efforts we are still not able to cure the majority of rheumatic diseases. A therapeutic challenge include chronicity of inflammation, autoimmunity, and degenerating muscular skeletal system. Although, rheumatic diseases differ in their immunopathology, they share common mechanisms of initiation and perpetuation. Moreover, there is a considerable translational potential for the understanding of other diseases involving the immune system, e.g. autoimmune diseases, allergy and infection. The diversity of rheumatic diseases, the multiplicity of tissues involved, i.e. bone, cartilage, joints, kidney, skin, blood vessels and the multidisciplinary approach require to understand the molecule basis of these diseases make their diagnosis very difficult.

Diagnosis of arthritis and other rheumatic diseases is often difficult, as many symptoms are similar among the different diseases. To make an accurate diagnosis, a physician may need to conduct a review of the medical history, perform a physical examination obtain laboratory tests, x-rays and other imaging tests. The rheumatic diseases are, e.g. rheumatoid arthritis, fibromyalgia, lupus erythematodes, polymyaglia rheumatica, progressive systemic sclerosis, Sjögren-Syndrome, systemic lupus ethematodes and joint inflammation.

The American College of Rheumatology has defined (1987) a number of criteria for the diagnosis of, e.g. rheumatoid arthritis. Morning stiffness of more than one hour, arthritis and soft tissue swelling of more than 3 of 14 joints/joint groups, arthritis of hand joints, symmetric arthritis, subcutaneous nodules in specific blazes, rheumatoid factor at a level above the 95 th/percentile and radiological changes suggested of joint erosion. At least four criteria have to be met to establish the diagnosis, although many patients are treated despite not meeting the criteria. When rheumatoid arthritis is being clinically suspected immunological studies are required such as rheumatoid factor (RF, a specific antibody). A negative RF does not rule out rheumatoid arthritis. Recently, a new serological test has been developed, which tests for the presence of so called anti-citrullinated protein (ACP) antibodies. Like RF, this test can detect approximately 80% of all RA patients, but is rarely positive in non-RA patients. Also, several other blood tests are usually done to allow for other causes of arthritis, such as lupus erythematosis. Such tests include the erythrocyte sedimentation rate (ESR), c-reactive protein, full-blood count, renal function, liver enzymes and immunological tests, e.g. antinuclear antibody/ANA are all performed at this stage.

As outlined for rheumatoid arthritis as one disease amongst those in the family of inflammatory rheumatic diseases, diagnosis in the field of diseases is difficult. Thus, there is a need for a safe and reliable diagnostic tool.

Artheriosclerosis is a disease affecting the arterial blood vessel. It is caused by the formation of multiple plagues within the artery.

Areas of severe narrowing, stenosis, detectable by angiography, and to a least extend "stress testing" have long been the focus of human diagnostic techniques for cardiovascular disease in general. However, these methods focus on detecting only severe narrowing, not the under-lying arterosclerosis disease. As demonstrated by human clinical studies, most severe events occur in locations with heavy plague, yet little or no lumen narrowing present before debilitating events suddenly occur. Plaque rupture can lead to artery lumen occlusion within seconds to minutes and potential permanent debility and sometimes sudden death. 77% lumen stenosis used to be considered by cardiologists as the hallmark of clinically significant disease because it is only at this severity of narrowing of the larger heart arteries that recurring episodes of angina and detectable abnormalities by stress testing methods are seen. However, clinical trials have shown that only about 14% of clinically debilitating events occur at locations with this, or greater severity of narrowing. The majority of events occur due to artheroma plague rupture at areas without narrowing sufficient enough to produce any angina or stress test abnormalities. Thus, there is an extreme need for a diagnostic method for diagnosing arteriosclerosis. Various different kinds of arteriosclerosis exist. Arteriosclerosis such as coronary arteriosclerosis, cerebral arteriosclerosis such as apoplexy and enzephalo malacia, diabetic nephrosclerosis and juvenile malign nephrosclerosis and Mönckeberg-Arteriosclerosis.

The present invention addresses the need for a diagnostic tool for the above-mentioned family of diseases. The present invention further addresses the need for a medicament for treating the above-mentioned diseases.

SUMMARY OF THE INVENTION

The present invention relates to a method for diagnosis of a disease selected from the group of diabetes, vasculitis, collagenosis, an inflammatory rheumatic disease and arteriosclerosis wherein, presence or absence of an anti-$AT_1$-receptor antibody is determined in a sample from a patient to be diagnosed and wherein, the presence of an Anti-$AT_1$-receptor antibody is indicative of the disease.

The inventors have found that more than ⅓ of patients (35%) with rheumatic diseases are positive for the presence of an anti-$AT_1$-antibody, whereas in patients without rheumatic disease only 8.3% have a detectable anti-$AT_1$-antibody.

Determination was performed in blind test fashion. All patients with rheumatic diseases displayed severe complications and were difficult to treat with standard methods. There was a clear correlation between the presence of the anti-$AT_1$ antibody and the disease complication.

In a preferred embodiment of the invention the determination of presence or absence of an anti-$AT_1$-receptor antibody is done by detecting one or more of the antibodies selected from the group of IgA-antibody, IgG-antibody and IgM-antibody and more in particular an IgG1, IgG2, IgG3 and IgG4 antibody.

In one embodiment of the invention the invention relates to an immunoassay. There are numerous ways of performing an immunoassay in a preferred embodiment of the invention, the immunoassay is a luciferase assay and/or an ELISA.

The invention further relates to the use of an $AT_1$-receptor-peptide or a functional analog thereof for the diagnosis of a disease and is selected from the group of vasculitis, collagenosis, and inflammatory rheumatic disease and arteriosclerosis.

The invention relates to a research and/or diagnostic kit for the diagnosis of a disease selected from the group of vasculitis, collagenosis, an inflammatory rheumatic disease and arteriosclerosis, wherein the kit comprises an $AT_1$-receptor-peptide or a functional analog thereof.

In a further embodiment the invention relates to the use of an inhibitor of an anti-$AT_1$-receptor-antibody or an inhibitor of an $AT_1$-receptor for the production of a medicament.

DETAILED DESCRIPTION OF THE INVENTION

The inventors have found that certain diseases may be diagnosed by detecting the presence or absence of an anti-$AT_1$-receptor antibody in a sample from a patient to be diagnosed. In fact, the inventors have found that 35% of patients which have a rheumatic disease are positive for the anti-$AT_1$-antibody. The same anti-$AT_1$-antibody may be detected only in 6.2% of the cases in patients with no rheumatic disease.

Thus, the present invention relates to a method for diagnosis of a disease, wherein presence or absence of an anti-$AT_1$-receptor antibody is determined in a sample from a patient to be diagnosed.

It has been possible to demonstrate that there is a relationship between the presence of said anti-$AT_1$-receptor antibody and the likelihood of diabetes, vasculitis, collagenosis, and inflammatory rheumatic disease and arteriosclerosis. It has been demonstrated that the presence of the anti-$AT_1$-receptor antibody gives rise to inflammatory rheumatic disease. Further, the presence of an anti-$AT_1$-receptor antibody is diagnostic for diabetes, vasculitis, collagenosis and arteriosclerosis.

In connection with the present invention, a number of general terms will be used as follows:

According to the invention "graft rejection" is to be understood to be induction of an immune reaction to the graft in the recipient. An immune reaction in the recipient is a specific protective or defense reaction of the body against the antigens of the transplant.

The "$AT_1$-receptor" may be present in its natural cellular environment and can be used together with the material associated with the receptor in its natural state as well as in isolated form with respect to its primary, secondary and tertiary structures, the $AT_1$-receptor is well known to those skilled in the art. Based on the weight of the whole receptor in the preparation to be used according to the invention, the isolated receptor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the $AT_1$-receptor can be used. Similarly, an $AT_1$-receptor produced by means of recombinant techniques, which receptor includes amino acid modifications, such as inversions, deletions, insertions, additions etc. can be used according to the invention provided that this part of the essential function of the $AT_1$-receptor is present, namely the capability of binding antibodies. The $AT_1$-receptor being used may also comprise exceptional amino acids and/or modifications of such as alkylation, oxidation, thiol-modification, denaturation, oligomerization and the like. The receptor can also be synthesized by chemical means. According to the invention the $AT_1$-receptor particularly can be a protein and/or peptide or a fusion protein, which in addition to other proteins, peptides or fragments thereof, includes the $AT_1$-receptor as a whole or in part. Using conventional methods, peptides or polypeptides of the $AT_1$-receptor which have functionally analogs, analogous properties can be determined by those skilled in the art. For example such polypeptides or peptides have 50-60%, 70% or 80%, preferably 90%, more preferably 95%, and most preferably 98% homology to peptides identified as $AT_1$-receptor, and said homology can be determined, e.g. by means of Smith-Waterman homology search algorithm, using the MPFRCH Programme (Oxford Molecular), for example.

The term "peptide" of an $AT_1$-receptor used in the present invention, comprises also molecules differing from the original sequence by deletion(s), insertion(s), substitution(s) and/or other modifications well known in the prior art and/or comprising a fragment of the original amino acid molecule, the $AT_1$-receptor still exhibiting the properties mentioned above. Also included are allele variants and modifications. Methods of producing the above changes in the amino acid sequence are well known to those skilled in the art and have been described in the standard textbooks of molecular biology, e.g. Sambrook et al. Supra. Those skilled in the art will also be able to determine whether an $AT_1$-receptor, thus, modified still has the properties mentioned above. Possible $AT_1$-receptor peptides used according to the invention can be, e.g. AVHYQSN (SEQ ID NO. 1); SHFYQTR (SEQ ID NO. 2) and/or GYYFDTN (SEQ ID NO. 3).

In the present specification all of the above illustrated modifications of the $AT_1$-receptor will be referred to as "functionally analogous peptides or proteins" in brief.

"Sample" in the meaning of the invention can be all biological tissues and fluids such as blood, lymph, urine, cerebral fluid. The sample is collected from the patient and subjected to the diagnosis according to the invention.

The "anti-$AT_1$-receptor antibody" in the meaning of the invention, which is to be detected, binds the $AT_1$-receptor in a specific fashion. The antibody can also be modified (e.g. oligomeric, reduced, oxidized and labeled antibodies). The term anti-$AT_1$-receptor antibody as used herein comprises both intact molecules and also anti-$AT_1$-receptor antibody fragments such as Fab, F(ab')$_2$ and Fv capable of binding specific epitope determinance of the $AT_1$-receptor. In these fragments the anti-$AT_1$-receptor antibody(ies) capability of selectively binding its antigen or receptor is retained in part, the fragments being defined as follows: (1) Fab, the fragment which contains a monovalent antigen-binding fragment of an antibody molecule, can be generated by cleavage of a whole antibody using the enzyme papaine, thereby obtaining an intact light chain and part of a heavy chain; (2) the Fab fragment of an antibody molecule can be produced by treatment of a whole antibody with pepsin and subsequent reduction, thereby obtaining an intact light chain and part of a heavy chain, two Fab fragments per anti-body molecule are obtained; (3) F(ab')$_2$ the fragment of the antibody which can be obtained by treatment of a whole antibody with the enzyme pepsin without subsequent reduction, F(ab')$_2$ is a dimer comprised of two Fab fragments held together by two disulfate bonds; (4) Fv defined as fragment modified by genetic engineering which includes the variable region of the light chain and the variable region of the heavy chain is expressed in the form of two chains; and (5) single-chain antibody (SCA) defined as a molecule modified by genetic engineering, which includes the variable region of the light chain and the variable region of the heavy chain, linked by a suitable polypeptide linker to perform a genetically fused single-chain molecule.

The term "epitope" as used in the present invention represents any antigen determinant on the $AT_1$-receptor. Epitope determinance normally consists of chemically active surface groups of molecules such as amino acids or sugar-side chains and normally has specific features of the free dimensional structure as well as specific chart properties.

The anti-$AT_1$-receptor antibody binds specifically to the $AT_1$-receptor or in doing so shows specific immuno reactivity when the anti-$AT_1$-receptor antibody assumes its function in a binding reaction in the presence of a heterogeneous population of $AT_1$-receptors or fragments thereof, thereby allowing a conclusion whether the $AT_1$-receptor or another biological structure is present. Under the present conditions of an immunoassay, the above-mentioned anti-$AT_1$-receptor antibodies will preferably bind to a specific portion of the $AT_1$-receptor, while no significant binding to other proteins present in the sample will take place.

"Patients" in the meaning of the invention are understood to be all persons, animals, plants or microorganisms, irrespective whether or not they exhibit pathological changes. In the meaning of the invention, any sample collected from cells, tissues, organs or the like can be a sample of a patient to be diagnosed. In a preferred embodiment the patient according to the invention is a human. In a further preferred embodiment of the invention the patient is a human suspected to have a disease selected from the group of vasculitis, collagenosis, an inflammatory rheumatic disease and arteriosclerosis.

An "immune reaction" in the meaning of the invention is a specific interaction between the $AT_1$-receptor or peptides or proteins of analogous function and anti-$AT_1$-receptor antibodies. The immune reaction can be detected using various immunoassays.

"immunoassays" in the meaning of the invention are assays utilizing the specific interaction between the $AT_1$-receptor and peptides or proteins of analogous function and the anti-$AT_1$-receptor antibodies, in order to detect the presence or determine the concentration of the anti-$AT_1$-receptor antibodies. For example, a detection in quantification of the anti-$AT_1$-receptor antibodies can be performed with the aid of said peptides or proteins of analogous function, e.g. by immuno precipitation or immuno blotting.

According to the invention the disease is selected from the group of diabetes, vasculitis, collagenosis, an inflammatory rheumatic disease and arteriosclerosis.

In a preferred embodiment the diabetes is a type I diabetes.

In a preferred embodiment the collagenosis is a diseases selected from the group of Lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome.

In a very preferred embodiment the collagenosis is systemic sclerosis.

In a preferred embodiment the inflammatory rheumatic disease is selected from the group of rheumatoid arthritis, fibromyalia, lupus erythematodes, polymyaglia rheumatica, progressive systemic sclerosis, Sjögren-syndrome, systemic lupus erythematodes, Raynaud-Syndrom (Morbus Raynaud) and joint inflammation.

In a very preferred embodiment the inflammatory rheumatic disease is progressive systemic sclerosis.

Further, in preferred embodiment the arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckeberg-arteriosclerosis.

In a very preferred embodiment the arteriosclerosis is diabetic nephrosclerosis.

In a preferred embodiment of the invention the determination of the presence or the absence of an anti-$AT_1$-receptor antibody is done by detecting one or more of the antibodies selected from the group of IgA-antibody, IgG-antibody and IgM-antibody.

Human antibodies can be divided into five classes of immunoglobulins. Class A immunoglobulin (IgA) exists in form which is dissolved in blood as well as in secretory variant. IgA comprises two basic classes. Secretory IgA consist of two immunoglobulin basic molecules, together with a J-chain and a secretory component. More, specifically IgA molecules can prevalent in body secretions.

Class IgG immunoglobulins represent the major part among the immunoglobulins. The anti-bodies of the secondary immune response taking place upon contact of the immune system of a particular antigen largely belong to the IgG class.

In a particularly preferred embodiment of the invention, the anti-$AT_1$-receptor antibody is selected from the group of IgG1, IgG2, IgG3 and IgG4.

"Immunoassays" in the meaning of the invention are assays utilizing the specific interaction between the $AT_1$-receptor and peptides or proteins of analogous function and the anti-$AT_1$-receptor antibody, in order to detect the presence or determine the concentration of the anti-$AT_1$-receptor antibodies. For example, the detection and quantification of the anti-$AT_1$-receptor antibody can be performed with the aid of said peptides or proteins an analogous function, e.g. by immunoprecipitation or immunoblotting. For example, immunoassays in the meaning of the invention can be subdivided into the following steps: (1) anti-$AT_1$-receptor antibody/$AT_1$-receptor reaction, (2) if required separation of the anti-$AT_1$-receptor antibody complex from other components of the reaction mixture especially from non-bound anti-$AT_1$-receptor antibodies an $AT_1$-receptor and (3) measuring the response. As for the anti-$AT_1$-receptor antibody/$AT_1$-receptor reaction various configurations of passable, e.g. (a) precipitation of one reaction with an access of the other or (b) competition between known quantities of anti-$AT_1$-receptor antibody or $AT_1$-receptor and the material to be investigated.

For example, an assay for anti-$AT_1$-receptor antibodies can be performed by a) using access $AT_1$-receptors/peptides or proteins of analogous function or b) competition between a labeled anti-$AT_1$-receptor antibody of known amount and non-labeled antibody of unknown amount for a defined quantity of $AT_1$-receptor or peptides of proteins of analogous function.

The $AT_1$-receptor can be immobilized on a solid support. To allow separation of the anti-$AT_1$-receptor antibody/$AT_1$-receptor complex. For example, the solid support material can be nitrocellulose, polyvinylchloride or polystyrene, e.g. the well of a microtiter plate. The immunoassay may take place in a microfluidic environment. To measure the anti-$AT_1$-receptor antibody/$AT_1$-receptor interaction, it is possible to use labeled anti-$AT_1$-receptor antibodies, labeled $AT_1$-receptors or secondary reagents, for example. The $AT_1$-receptor can be labeled radioactively or with enzymes or with fluorescent compounds, for example. Irrespective of the label that is used, the response of the anti-$AT_1$ receptor antibody/$AT_1$-receptor interaction can be enhanced by utilizing the affinity of the proteins avidine or streptavidine for biotin. The immunoassays used according to the invention can be: (1) immunoassays using radioactive label: (a) radioimmunoassay with competitive binding (RIA) and (b) immunoradiometric assay (IRMA); (2) immunoassays using an enzyme label: (a) enzyme immunoassays (EIA) and (b) enzyme-linked immunosorbenassys (ELISA); (3) immunoassays using a combination of radioisotope and enzyme labels (ultrasensitive enzyme radio immunoassay) (USERIA). Further, the immunoassay according to the invention may be a fluorescent immunoassay, a chemiluminescent assay, an agglutination assay, a nephelometric assay, a turbidimetric assay, a Western Blot, a competitive immunoassay, a non-competitive immunoassay, a homogenous immunoassay, a heterogenous immunoassay, a reporter-assay, e.g. a luciferase assay.

In a preferred embodiment of the invention the immunoassay is an ELISA.

The invention also relates to the use of an $AT_1$-receptor-peptide or a functional analog thereof for the diagnosis of a disease selected of the group of diabetes, vasculitis, collagenosis, an inflammatory rheumatic disease and arteriosclerosis.

In a preferred embodiment the diabetes is a type I diabetes.

Further, in a preferred embodiment in the use according to the invention, the collagenosis is a disease selected from the group of lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-Syndrome. The inflammatory rheumatic disease is selected from the group of rheumatoid arthritis, fibromygalia, lupus erythematodes, polymyaglia rheumatica, progressive systemic sclerosis, Sjögren-syndrome, systemic lupus erythematodes and joint inflammation. The arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

The invention further relates to a research and/or diagnostic kit for the diagnosis of a disease selected from the group of diabetes, vasculitis, collagenosis, an inflammatory rheumatic disease and arteriosclerosis, wherein the kit comprises an $AT_1$-receptor peptide or a functional analog thereof.

It is preferred that the diabetes is type I diabetes.

In a preferred embodiment the research and/or diagnostic kit comprises an $AT_1$-receptor-peptide or a functional analog thereof.

In a preferred embodiment the research and/or diagnostic kit according to the invention is for the diagnosis of a collagenosis disease is selected from the group of lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome, the inflammatory rheumatic disease is selected form the group of rheumatoid arthritis, fibromygalia, lupus erythematodes, polymyaglia rheumatica, progressive systemic sclerosis, Sjögren-syndrome, systemic lupus erythematodes and joint inflammation, and the arteriosclerosis is selected from the group of arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

The immunological test kit according to the invention comprises the $AT_1$-receptor or a functional analog thereof or peptides or proteins of analogous function per se. The test kit of the invention comprises at least one complete $AT_1$-receptor or functionally analogous peptides or proteins of said receptor, optionally bound to a solid phase. Furthermore, the test kit may also comprise buffers, specific conjugate together with an enzyme, wash solution, substrate solution to detect the immune reaction and/or a quenching solution. Using these substances a person skilled in the art will be able to perform, e.g. an ELISA to detect the anti-$AT_1$-receptor antibodies. The buffers, specific conjugate plus enzyme, wash solution, substrate solution to detect immune reaction and quenching solution are well known to those skilled in the art. For example, it would be sufficient to have the test comprise a freeze-dried $AT_1$-receptor or peptides or proteins of $AT_1$-receptor analogous function and to add the buffers and other solutions immediately prior to testing the biological material. However, it is also possible to provide the test kit with the $AT_1$-receptor or its functionally analogous peptides of proteins bound to a solid phase. To detect the anti-$AT_1$-receptor antibodies the specific conjugate, wash solution, substrate solution and quenching solution, which can be components of the test kit, have to be added according to a mode well known to those skilled in the art.

In another advantageous embodiment of the invention, it is envisioned that the test kit is a test strip comprising the $AT_1$-receptor or its functionally analogous peptides or proteins immobilized on a solid phase. For example, the test strip can be immersed in serum or other patient samples and incubated.

Using a specific biochemical reaction on the test strip after formation of the $AT_1$-receptor/anti-$AT_1$-receptor antibody complex, a specific colour reaction can be triggered by means of which the anti-$AT_1$-receptor antibody can be detected.

The test system of the invention permits quantification of the anti-$AT_1$-receptor antibodies directly in a sample, e.g. in plasma of patients. The detection method according to the invention is time saving and cost effected. Large amounts of the samples can be tested and, owing to the low amount of the equipment required, routine laboratories can be used.

The invention also relates to an inhibitor of an anti-$AT_1$-receptor antibody and an inhibitor of an $AT_1$-receptor for the production of a medicament.

The term "inhibitor" refers to an agent that binds to the receptor but does not provoke the normal biological response. For example, an inhibitor may be any molecule which, when bound to an $AT_1$-receptor, decreases the activity of or reduces the expression levels of the $AT_1$-receptor.

In a preferred embodiment the medicament is for the treatment of a disease selected from the group of diabetes, vasculitis, collagenosis, an inflammatory rheumatic disease and arteriosclerosis. It is preferred that the diabetes is type I. In particular preferred embodiment the collagenosis is a disease selected from the group of selected lupus erythematodes disseminatus, systemic sclerosis, eosinophilia infectiosa, polymyositis, dermatomysistis, periarteriitis nodosa, rheumatoid arthritis, Wegener-granulomatose, CREST-syndrome and SHARP-syndrome, the inflammatory rheumatic disease is selected form the group of rheumatoid arthritis, fibromygalia, lupus erythematodes, polymyaglia rheumatica, progressive systemic sclerosis, Sjögren-syndrome, systemic lupus erythematodes and joint inflammation, and the arteriosclerosis is selected from the group of arteriosclerosis is selected from the group of central arteriosclerosis, coronary arteriosclerosis, cerebral arteriosclerosis such as apoplexy and encephalomalacia, nephrosclerosis such as diabetic nephrosclerosis and juvenile malign nephrosclerosis and Mönckenberg-arteriosclerosis.

In a preferred embodiment the inhibitor of the $AT_1$-receptor or the anti-$AT_1$-receptor antibody is selected from the group of
(i) losartan (1-((2'-(2H-tetrazol-5-yl)biphenyl-4-yl)methyl)-2-butyl-4-chloro-1H-imidazol-5-yl)methanol) an inhibitor of the $AT_1$-receptor,
(ii) candesartan (3-((2'-(2H-tetrazol-5-yl)biphenyl-4-yl)methyl)-2-ethoxy-3H-benzo[d]imidazole-4-carboxylic acid) an inhibitor of the $AT_1$-receptor,
(iii) eprosartan (4-[[2-butyl-5-(2-carboxy-3-thiophen-2-yl-prop-1-enyl)-imidazol-1-yl]methyl]benzoic acid) an inhibitor of the $AT_1$-receptor,
(iv) irbesartan (2-butyl-3-[p-(o-1H-tetrazol-5-ylphenyl)benzyl]-1,3-diazaspiro[4.4]non-1-en-4-one) an inhibitor of the $AT_1$-receptor,
(v) olmesartan an inhibitor of the $AT_1$-receptor,
(vi) telmisartan (2-[4-[[4-methyl-6-(1-methylbenzoimidazol-2-yl)-2-propyl-benzoimidazol-1-yl]methyl]phenyl] benzoic acid) an inhibitor of the $AT_1$-receptor,
(vii) valsartan an inhibitor of the $AT_1$-receptor,
(viii) an anti-sense molecule directed against the $AT_1$-receptor or the anti-$AT_1$-receptor antibody,
(ix) antibodies against the $AT_1$-receptor,
(x) antibodies against the anti-$AT_1$-receptor antibody, and
(xi) a nucleic acid molecule that results in silencing $AT_1$-receptor activity through, RNAi such as dsRNA.

Plasmapheresis (from the Greek plasma, something molded, and apheresis, taking away) is the removal of (components of) blood plasma from the circulation. It is used as a therapy in particular diseases, and it is also a method by which blood donors donate only plasma, with remaining red cells and platelets returned to their circulatory systems, allowing up to twice weekly plasma donations.

An important use of plasmapheresis is in the therapy of autoimmune disorders, where the symptoms are so catastrophic that medical therapy is insufficient in controlling the symptoms. Plasmapheresis clears antibodies from circulation.

Other uses are the removal of blood proteins where these are overly abundant and cause hyperviscosity syndrome.

In one embodiment of the invention the invention relates to method for the removal anti-$AT_1$-receptor antibody, wherein in a first step the presence or absence of an anti-$AT_1$ receptor anti-body is determined in a blood sample from a patient to be diagnosed wherein the patient is thought to have a disease selected from the group of vasculitis, collagenosis, an inflammatory rheumatic disease and arteriosclerosis wherein upon determining the presence of an anti-$AT_1$-receptor antibody the blood of the patient is subjected to a plasmapheresis.

Plasmapheresis may be performed multiple times in a preferred embodiment it is performed in intervals of 4 weeks until the titre of the anti-$AT_1$-antibody is below detection level.

EXAMPLES

Example I $AT_1$-Receptor ELISA

A suitable streptavidine-coated microtiter plate is loaded with the biotinylated peptide encoding the $AT_1$-receptor.

Such peptides may be AVHYQSN (SEQ ID NO. 1), SHFYQTR (SEQ ID NO. 2) and/or GYYFDTN (SEQ ID NO. 3).

To this end, 100 µl of a solution per well in the microtiter plate is incubated with 5 µg/ml in a suitable dilution buffer. To measure the non-specific binding, wells are also filled with 100 µl of dilution buffer. The dilution buffer may comprise 0.5% bovine serum albumin, 10 mM phosphate buffer (pH 7.4), 140 mM NaCl and 0.05% TWEEN 20.

Subsequent to the time period of reaction, the peptide solution is moved by decanting and each well is washed three times with 250 µl of a suitable wash buffer. A suitable wash buffer may comprise 10 mM phosphate buffer (pH 7.4), 140 mM NaCl and 0.1% TWEEN 20. Thereafter, 100 µl per well of sera are diluted in a dilution buffer and placed on both the peptide-loaded and comparative plates are incubated. Subsequently, the wells are washed as described above.

The bound antibodies are detected using goat-anti-human immunoglobulin G-antibody having peroxidase coupled thereto. To this end, the antibody is diluted in dilution buffer and incubated (100 µl/well), and this is followed by three wash steps (see above).

Following addition of 100 µl over ready-for-use substrate solution (e.g. 3,3',5,5'-tetramethylbenzidine), the colour develops depending on the amount of peroxidase in the well. The substrate reaction is determined by addition of 100 µl of 0.5 M sulfuric acid. The absorption is measured at 450 nm For evaluation the difference between the absorptions of peptide-loaded microtiter plate and comparative plate with no peptide is formed. Samples having higher absorption then the cut-off are positive. The cut-off is calculated from the mean value of the absorption of negative donors plus three times the standard deviation. In general, a cut-off control or a standard dilution series allowing quantification in relative units is co-performed in the test.

Example II

Various patient groups (with positive diagnosis) as well as controls were tested with respect to the presence or absence of the anti-$AT_1$-receptor antibody. Table I shows the result obtained.

TABLE I

| Disease | Presence of anti-$AT_1$-receptor antibody in % |
|---|---|
| rheumatic disease | 35 |
| Patients without inflammatory rheumatic disease | 8.3 |

Example III

We analyzed sera of 212 patients with systemic sclerosis (SSc), 60 healthy control subjects, 120 rheumatoid arthritis patients and 124 additional control subjects with either morphea, primary Raynaud phenomenon or idiopathic pulmonary hypertension for the presence of anti-bodies directed against angiotensin II type 1 receptor ($AT_1R$) and endothelin-1 type A receptor ($ET_AR$) by a solid phase assay. Individual organ involvement, patient survival and the effect of immunosuppressive or cell therapies were also assessed. Vascular responsiveness to natural receptor ligands, Angiotensin II and Endothelin-1 was studied ex vivo in pulmonary resistance arteries.

$AT_1R$-AA was detected in 56.6% of the SSc patients, respectively, but only in 9.6% subjects with control diseases, and 2.8% of the normal subjects. Patients with $AT_1R$-AA had more severe disease. Positivity for $AT_1R$-AA strongly predicted development of pulmonary arterial hypertension and SSc-related mortality. The antibody levels were not influenced by commonly used immunosuppression or stem-cell transplantation. Stimulation of pulmonary resistance vessels with $AT_1R$-AA ex vivo increased the vasoconstrictive responsiveness towards Endothelin-1 and Angiotensin II that could be blocked by corresponding receptor antagonists.

Patients and Assessment of Clinical Manifestations

Serum samples were collected in 212 consecutive patients with scleroderma between January 2004 and November 2006. Patients had limited (n=89), diffuse SSc (n=78), or an overlap syndrome (n=45) with other connective tissue diseases as defined by LeRoy et al, and met by American College of Rheumatology criteria for the classification of SSc (21, LeRoy-EC, J. Rheumatol. 1988, Massi). We obtained control sera from 71 healthy subjects and 239 control disease patients including 115 rheumatoid arthritis patients, 33 patients with morphea, 31 patients with primary Raynaud's phenomenon, and 60 patients with idiopathic pulmonary arterial hypertension. The diagnosis in each control group was made according to established criteria for each condition. Written informed consent to use serum samples for research purpose was obtained from each patient.

We also studied 11 random patients with early diffuse systemic sclerosis before initiation of intravenous cyclophosphamide pulse therapy (750 mg/m$^2$ per pulse), 3 patients treated with rituximab and recipients of autologous stem cell transplants included in the ASTIS trial (Laar). First samples were obtained before initiation of therapy and up to seven control samples during 24 months follow-up.

A procedure standardized by European Scleroderma Trials and Research group (EUSTAR) was used to collect data on all patients, and the following variables were collected within the first months of follow-up after serum sampling. Skin fibrosis was assessed by at least two independent investigators with the use of modified Rodnan skin score. The haemoglobin level and ESR were derived from blood samples. Serum was analyzed for the presence of anti-centromere antibodies (ACA), antitopoisomerase antibodies (Scl-70), anti-$AT_1R$ and the anti-$ET_AR$-autoantibodies. Lung function was assessed by the predicted forced vital capacity (FVC) and the diffusion capacity adjusted for haemoglobin concentration (DLCO) by a single breath method. Patients with pathologic pulmonary lung function test were examined by a high resolution CT scan; the remaining patients had a chest X-ray. Cardiac involvement was confirmed by a physician if two of the following changes: diastolic dysfunction, ECG changes, decreased ejection fraction, or palpitations were present.

PAH secondary to SSc was suspected in patients with progressive dyspnoea at moderate exercise (NYHA III), >25 mmHg pulmonary artery systolic pressure by echocardiography, >1.4-fold increase of the FVC/DLCOcSB ratio, or signs of right ventricular failure as assessed by echocardiography (e.g. pericardial effusion, increased diameters of the right ventricle). PAH was considered as proven by >25 mmHg mean pulmonary arterial pressure (mPAP) at rest or $\geq$35 mmHg at exercise in the presence of pulmonary vascular resistance >3 mmHg/L/min and a pulmonary capillary wedge pressure <15 mmHg by right heart catheterizations. Deaths and resuscitations were only included into the study when related to SSc.

Solid Phase Assay

Anti-$AT_1R$ and the anti-$ET_1R$-autoantibodies were measured by a cell-ELISA. The test employs membrane extracts of either $AT_1R$ or the $ET_AR$ overexpressing CHO cells serving as a solid phase. The specificity of the anti-$AT_1R$ and the anti-$ET_AR$-ELISA was proven by blocking experiments using membrane extracts from the corresponding cell lines showing a dose-dependent and antigen-restricted decrease in the antibody binding for respective antigens. In contrast, membrane extracts from non-transfected CHO cells had no blocking effect on the $AT_1R$ and the anti-$ET_AR$ antibody binding.

Cut-off and inter-assay variability: Serum specimens were randomly ordered for analysis and assays were performed by personnel who were unaware of the patients' pathology. All tests were conducted in duplicate for both, the anti-$AT_1R$ and the anti-$ET_AR$ antibody.

Statistics

Receiver-operating-characteristic (ROC) curves were plotted for the sensitivity of the $AT_1R$-and $ET_AR$ antibody detection tests against 1 minus the specificity for all diseases studied and respective cut-off values were determined. Continuous data are presented as medians (with ranges). We performed comparisons between groups with use of Mann-Whitney U test for continuous variables. Additionally, hazard ratios were assessed by Kaplan-Meyer analyses for the first manifestation of pulmonary hypertension, digital ulcers, and death or resuscitation during the observation period. Odds ratios and relative risk were calculated to determine associations with individual organ involvements. Small vessel myography data were analyzed by ANOVA. A P value less than 0.05 was considered significant. Results are expressed as means ±SEM, n stands for the number of the studied pulmonary artery ring segments.

$ET_AR$ and $AT_1R$ Autoantibodies in Different Diseases

Figure 1A:
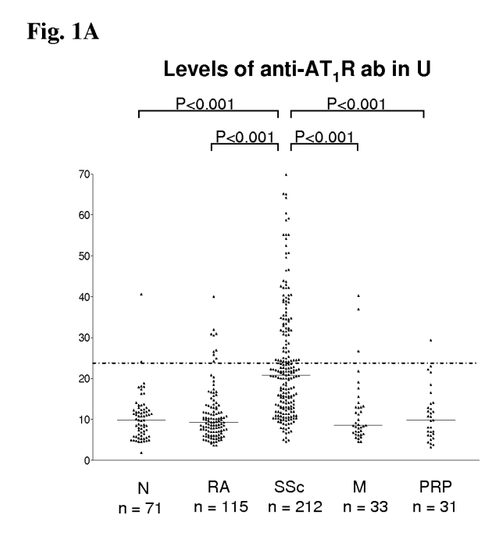
Figure 1B:
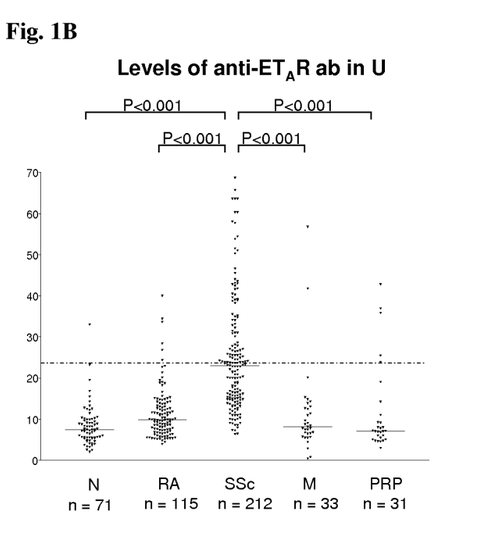

Among 212 SSc patients, 120 (56.6%), showed increased mean levels (24 U by CI 95% 21.7-25.4 U) of $AT_1R$ autoantibodies (AA) (FIG. 1, panel A). In contrast only 2 of 71 (2.8%) normal subjects, 11 of 115 RA patients (9.6%), 2 of 33 patients with morphea (6.1%), and 4 of 31 patients (12.9%) with primary Raynaud's phenomenon had $AT_1R$-AA. $ET_AR$-AA (FIG. 1, panel B) were detected in 123 of the 212 SSc (57.6%), but in only 2.8% of the normal subjects, 8.7% of the RA patients, 9.1% of the patients with morphea, and 12.9% of the patients with primary Raynaud's phenomenon. The majority of our patients (84%) had both $AT_1R$-AA and $ET_AR$-AA ($P<0.001$, $r^2=0.75$, FIG. 1, panel B). Singular positivity for $AT_1R$-AA was detected in 6% of SSc patients and in 10% for $ET_AR$-AA only.

Patients with diffuse SSc were more frequently positive for both autoantibodies and their presence was negatively correlated with the limited disease. Particularly, the risk to have proven or suspected PAH was increased in the $AT_1R$-AA and $ET_AR$-AA positive SSc patients (Table II). Among 32 patients with proven PAH and diffuse Ssc, 30 were both $AT_1R$-AA and $ET_AR$-AA positive. Despite the inverse correlation of $AT_1R$-AA and $ET_AR$-AA with limited Ssc, all patients with PAH and limited Ssc were autoantibody positive. 12 out of the 39 patients (30.7%) with limited systemic sclerosis and either $AT_1R$ or the $ET_AR$ antibodies suffered from PAH, but none of the 50 patients with limited disease without these antibodies. patients with limited systemic sclerosis and $AT_1R$ antibodies are of high risk to get PAH. Digital ulcers, lung fibrosis, anti-Scl70 positivity, and contractures were more frequent in $AT_1R$-AA and $ET_AR$-AA positive patients (Table II).

TABLE II $AT_1R$-AA and $ET_AR$-AA positivity and disease manifestations determined by clinical and laboratory parameters.

| | Months after Ab detection | | | | | | | |
|---|---|---|---|---|---|---|---|---|
| | 0 | 5 | 10 | 15 | 20 | 25 | 30 | 35 |
| Anti-AT1R + patients at risk | 110 | 104 | 91 | 82 | 72 | 60 | 35 | 5 |
| Anti-AT1R − patients at risk | 82 | 82 | 63 | 52 | 40 | 25 | 11 | 0 |

The association between anti-receptor antibody positive patients and lung fibrosis was also supported by analyzing lung function parameters. Percentage of predicted FVC and DLCO were lower in the antibody positive patient group when compared to the negatively tested patients. The higher degree of fibrotic changes in the antibody positive cohort was also emphasized by the higher modified Rodnan skin score in the antibody positive group. Patients with anti-receptor antibodies have also a longer disease course and have a higher ESR when compared to the vascular receptor autoantibody negative group (Table II).

PAH and Relation of Both Antibodies

Figure 2A:
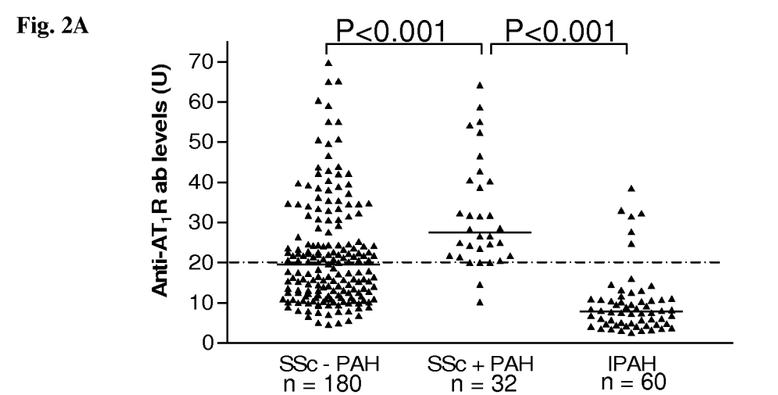
Figure 2B:
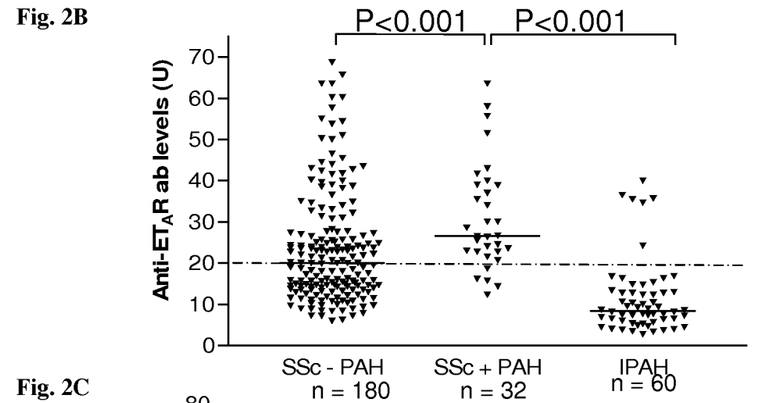
Figure 2C:
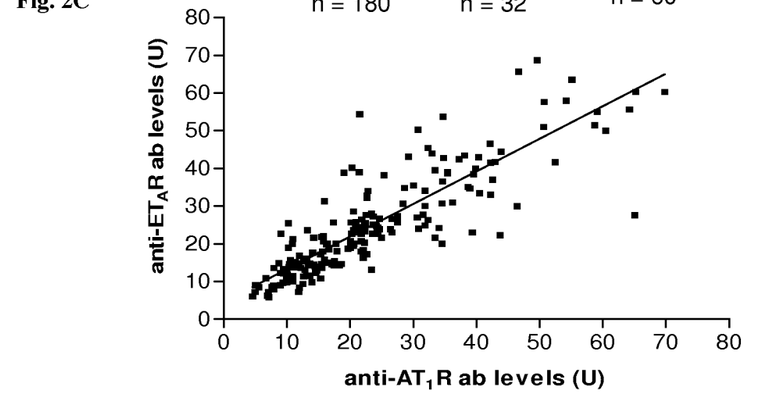

In addition to the high prevalence of PAH in patients with anti-$AT_1R$ or anti-$ET_AR$ antibodies the levels of both the anti-receptor antibodies were higher in patients with SSc-related PAH when compared to SSc patients without PAH (FIGS. 2A, B). In contrast, patients with idiopathic PAH revealed no increased frequency of antibodies against the receptors (10% of the 60 patients). The levels of both anti-$AT_1R$ or anti-$ET_AR$ antibodies in IPAH patients were lower when compared to patients with PAH related to SSc.

Predictive Value

Figure 3A:
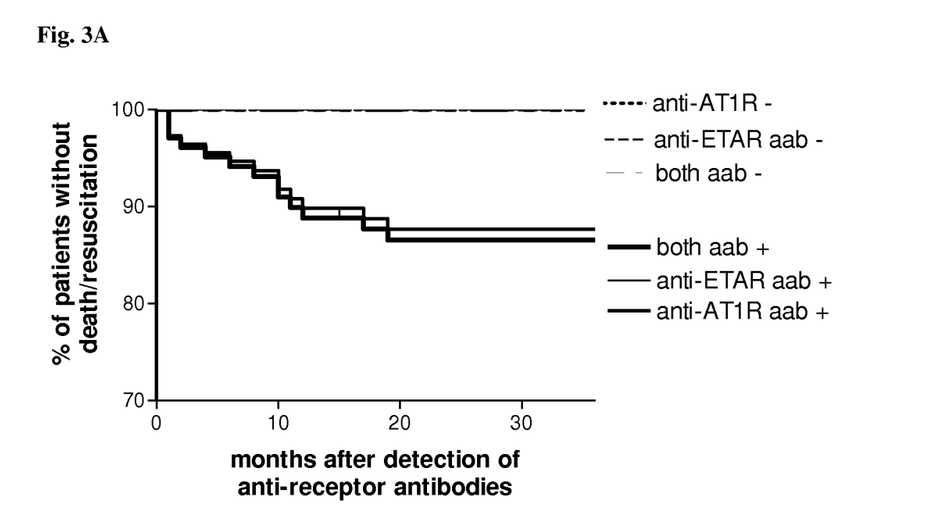

To determine the predictive value of both anti-$AT_1R$ and anti-$ET_AR$ autoantibodies, we have performed a prospective analysis for SSc-related mortality and PAH after the antibody analysis (FIG. 3A). Anti-$AT_1R$ antibodies and anti-$ET_AR$ antibodies have both a predictive value for mortality ($P=0.002$ and $P=0.001$, respectively) during a mean observation period of 22 months. 14 out of the 110 SSc patients with either anti-$AT_1R$ or anti-$ET_AR$ antibodies died (N=11) or have been resuscitated (N=3), but no single patient in the antibody negative group ($P=0.004$). SSc-related causes of death were multiorgan failure with and without PAH(N=7), PAH(N=3), and cardiac involvement with ventricular tachycardia (N=4).

Figure 3B:
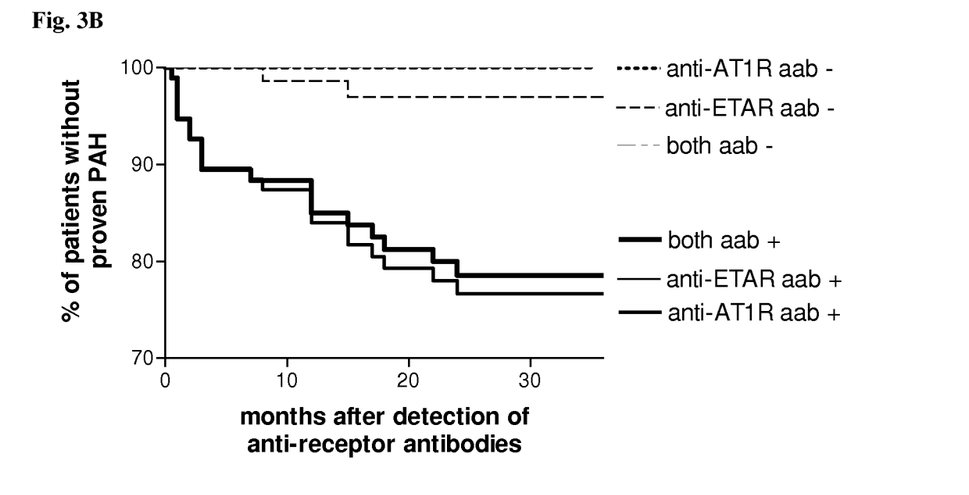

Furthermore, the anti-receptor antibodies also predict pulmonary arterial hypertension. During the observation period, diagnosis of PAH was made in 21 patients with either anti-$AT_1R$ anti-bodies but not in a single patient without anti-$AT_1R$ antibodies ($P<0.001$, FIG. 3B). Similar results were also obtained for the anti-$ET_AR$ antibody positive patients ($P<0.001$). The two patients negative for anti-$ET_AR$ antibodies but developing PAH were positive for the anti-$AT_1R$ antibodies and show anti-$ET_AR$ antibodies above 16 U. For patients that have both anti-receptor antibodies, the incidence of proven PAH was also increased ($P<0.001$).

Figure Captions

FIG. 1: Levels and diagnostic value of $AT_1R$-AA and $ET_AR$-AA autoantibodies in different autoimmune pathologies. $AT_1R$— (Panel A) and $ET_AR$-autoantibodies (Panel B) levels measured in serum of healthy control subjects (N), patients with rheumatoid arthritis (RA), systemic sclerosis (SSc), morphea (M), and primary Raynaud's phenomenon (PRP). Median levels are shown as lines; dotted lines represent the upper normal ranges Compared to the anti-body levels found in systemic sclerosis, all other diseases revealed lower levels ($P<0.001$). The levels of $AT_1R$ and $ET_AR$-autoantibodies show strong correlation ($P<0.001$, $r^2=0.74$).

FIG. 2: Comparison of $AT_1R$-(Panel A) and $ET_AR$-autoantibodies levels in SSc patients with PAH, SSc patients without PAH or patients with IPAH FIG. 3: Kaplan-Meier Curves to analyze the prospective value of anti-$AT_1R$ and anti-$ET_AR$ antibodies. SSc patients with anti-$AT_1R$, anti-$ET_AR$ antibodies, or with both anti-receptor antibodies are at higher risk for SSc-related mortality (panel A) as defined either by death (n=12) or resuscitation (n=3) and are at higher risk for PAH (panel B) during a mean observation period of 22 months. Notice that Y axes start at 70%.

The invention claimed is:

1. A method of predicting the pressure of systemic sclerosis in a human patient by determining anti-$AT_1$ receptor antibody level in a biological sample from the human patient comprising:
   (i) obtaining a biological sample from a human patient suspected of having systemic sclerosis;
   (ii) measuring anti-$AT_1$ receptor antibody level in the biological sample from the patient suspected of having systemic sclerosis; and
   (iii) comparing the anti-$AT_1$ receptor antibody level in the biological sample from the human patient suspected of having systemic sclerosis with anti-$AT_1$ receptor antibody levels from a healthy control subject and from one or more control disease subjects having rheumatoid arthritis, morphea, and primary Raynaud's phenomenon,
   wherein if the anti-$AT_1$ receptor antibody level in the biological sample from the human patient suspected of having systemic sclerosis is greater than the median anti-$AT_1$ receptor antibody levels in the healthy control subject and the control disease subjects having rheumatoid arthritis, mophea, and primary Raynaud's phenomenon, it is predictive of the presence of systemic sclerosis in the human patient.

2. The method according to claim 1, wherein the anti-$AT_1$ receptor antiboby level in the biological sample is about 2× the anti-$AT_1$ receptor antibody levels in the healthy control subject and the control disease subjects having rheumatoid arthritis, morphea, and primary Raynaud's phenomenon.

3. The method according to claim 1, wherein the anti-$AT_1$ receptor antibody level in the biological sample is about 2× to about 7× the anti-$AT_1$ receptor antibody levels in the healthy control subject and the control disease subjects having rheumatoid arthritis, morphea, and primary Raynaud's phenomenon.

4. The method according to claim 1, wherein the anti-$AT_1$ receptor antibody level in the biological sample is about 3× the anti-$AT_1$ receptor antibody levels in the healthy control subject and the control disease subjects having rheumatoid arthritis, morphea primary Raynaud's phenomenon.

5. The method according to claim 1, wherein the anti-$AT_1$ receptor antibody level in the biological sample is about 4× the anti-$AT_1$ receptor antibody levels in the healthy control subject and the control disease subjects having rheumatoid arthritis, morphea, and primary Raynaud's phenomenon.

6. The method according to claim 1, wherein the anti-$AT_1$ receptor antibody level in the biological sample is about 5× the anti-$AT_1$ receptor antibody levels in the healthy control subject and the control disease subjects having rheumatoid arthritis, morphea, and primary Raynaud's phenomenon.

7. The method according to claim 1, wherein the anti-$AT_1$ receptor antibody level in the biological sample is about 6× the anti-$AT_1$ receptor antibody levels in the healthy control subject and the control disease subjects having rheumatoid arthritis, morphea, and primary Raynaud's phenomenon.

8. The method according to claim 1, wherein the anti-$AT_1$ receptor antibody level in the biological sample is about 7× the anti-$AT_1$ receptor antibody levels in the healthy control subject, and the control disease subjects having rheumatoid arthritis, morphea, and primary Raynaud's phenomenon.

9. The method according to claim 1, wherein the anti-$AT_1$ receptor antibody level is the level of of one or more of the antibodies selected from the group of IgA-antibody, IgG-antibody and IgM-antibody.

10. The method according to claim 9, wherein the IgG-antibody is selected from the group consisting of IgG1, IgG2, IgG3 and IgG4.

11. The method according to claim 1, wherein the anti-$AT_1$ receptor antibody level is measured using an immunoassay.

12. The method according to claim 11, wherein the immunoassay is selected from the group consisting of immunoprecipitation, enzyme immunoassay (EIA), radioimmunoassay (RIA) or fluorescencent immunoassay, a chemiluminescent assay, an agglutination assay, nephelometric assay, turbidimetric assay, a Western blot, a competitive immunoassay, a noncompetitive immunoassay, a homogeneous immunoassay a heterogeneous immunoassay, a bioassay, an ELISA assay, and a reporter-assay such as a Luciferase-Assay.

13. The method according to claim 12, wherein the immunoassay is an ELISA assay.

* * * * *

UNITED STATES PATENT AND TRADEMARK OFFICE
CERTIFICATE OF CORRECTION

PATENT NO. : 8,425,877 B2
APPLICATION NO. : 12/376164
DATED : April 23, 2013
INVENTOR(S) : Schulze-Forster et al.

It is certified that error appears in the above-identified patent and that said Letters Patent is hereby corrected as shown below:

In the Claims

In claim 1, column 14, line 47, delete "pressure" and insert --presence-- therefor.

In claim 1, column 15, line 1, delete "mophea" and insert --morphea-- therefor.

In claim 2, column 15, line 5, delete "antiboby" and insert --antibody-- therefor.

In claim 4, column 15, line 19, after "morphea", insert --, and--.

In claim 9, column 16, line 11, delete "of of" and insert --of-- therefor.

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,425,877 B2
APPLICATION NO. : 12/376164
DATED : April 23, 2013
INVENTOR(S) : Schulze-Forster et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this
Ninth Day of December, 2014

Michelle K. Lee
*Deputy Director of the United States Patent and Trademark Office*